US006156320A

United States Patent [19]
Izvekova et al.

[11] Patent Number: 6,156,320
[45] Date of Patent: Dec. 5, 2000

[54] FERMENTED MILK NUTRACEUTICALS

[75] Inventors: Tamara Georgievna Izvekova, Erevan; Alexandr Viktorovich Kornilov, Vladimir; Irina Surenovna Amirian, Erevan, all of Russian Federation

[73] Assignee: Harry Parsekian, Boston, Mass.

[21] Appl. No.: 08/986,007

[22] Filed: Dec. 5, 1997

Related U.S. Application Data

[63] Continuation of application No. 08/511,875, Aug. 4, 1995.

[30] Foreign Application Priority Data

Feb. 5, 1993 [RU] Russian Federation ............. 93002600

[51] Int. Cl.$^7$ .................................................. A61K 39/385
[52] U.S. Cl. .................................... 424/197.11; 424/246.1
[58] Field of Search ............................... 424/489, 93, 92, 424/246.1, 197.11

[56] References Cited

U.S. PATENT DOCUMENTS

| | | |
|---|---|---|
| 3,480,443 | 11/1969 | Hata et al. . |
| 3,985,901 | 10/1976 | Hata et al. . |
| 4,314,995 | 2/1982 | Hata et al. . |
| 4,839,281 | 6/1989 | Hata et al. . |

FOREIGN PATENT DOCUMENTS

| | | |
|---|---|---|
| 2 290 846 | 6/1976 | France . |
| 2 492 227 | 4/1982 | France . |
| 1 492 779 | 10/1973 | Germany . |
| 475 714 | 9/1969 | Switzerland . |

OTHER PUBLICATIONS

Hilton, E. et al., "Ingestion of Yogurt Containing *Lactobacillus acidophilus* as Prophylaxis for Candidal Vaginitis" *Annals of Internal Medicine*, vol. 116, pp. 353–356, 1992.

Kneifel, W. et al., "Microflora and acidification properties of yogurt and yogurt–related products fermented with commercially available starter cultures" *International Journal of Food Microbiology*, vol. 18, pp. 179–189, 1993.

Hosoda, M. et al., "Studies on antimutagenic effect of milk cultured with lactic acid bacteria on the Trp–P2–induced mutagenicity to TA98 strain of *Salmonella typhimurium*" *Journal of Diary Research*, vol. 59, pp. 543–549, 1992.

Gilliland, S.E., Acidophilus Milk Products: A Review of Potential Benefits to Consumers *J. Dairy Sci*, vol. 72, pp. 2483–2494, 1989.

Lidbeck, A. et al., Lactobacilli, anticarcinogenic activities and human intestinal microflora *European Journal of Cancer Prevention*, vol. 1, pp. 341–353, 1992.

Chauvière, G. et al., "Adhesion of human *Lactobacillus acidophilus* strain LB to human enterocyte–like Caco–2 cells" *Journal of General Microbiology*, vol. 138, pp. 1689–1696, 1992.

Coconnier, M., et al., "Protein–Mediated Adhesion of *Lactobacillus acidophilus* BG2FO4 on Human Enterocyte and Mucus–Secreting Cell Lines in Culture" *Applied and Environmental Microbiology*, vol. 58, pp. 2034–2039, 1992.

Dong, M., et al., "Effects of Feeding Lactobacillus GG on Lethal Irradiation in Mice" *Diagn. Microbiol. Infect. Dis.*, vol. 7, pp. 1–7, 1987.

Elo, S. et al., "Attachment of *Lactobacillus casei* strain GG to human colon carcinoma cell ine Caco–2: comparison with other dairy strains" *Letters in Applied Microbiology*, vol. 13. pp. 154–156, 1991.

Goldin, B.R. et al., "Survival of Lactobacillus Species (Strain GG) in Human Gastrointestinal Tract" *Digestive Diseases and Sciences*, vol. 37, pp. 121–128, 1992.

Kaila, M., et al., "Viable versus inactivated lactobacillus strain GG in acute rotavirus diarrhoea" *Archives of Disease in Childhood*, vol. 72, pp. 51–53, 1995.

Kaila, M. et al., "Enhancement of the Circulating Antibody Secreting Cell Response in Human Diarrhea by a Human Lactobacillus Strain" *Pediatric Research*, vol. 32, pp. 141–144, 1992.

Isolauri, Erika et al., "Diet during Rotavirus Enteritis Affects Jejunal Permeability to Macromolecules in Suckling Rats" *Pediatric Research*, vol. 33, pp. 548–553, 1993.

Isolauri, E. et al., "Oral Bacteriotherapy for Viral Gastroenteritis" *Digestive Diseases and Sciences*, vol. 39, pp. 2595–2600, 1994.

Isolauri, E. et al., "*Lactobacillus casei* Strain GG Reverses Increased Intestinal Permeability induced by Cow Milk in Suckling Rats" *Gastroenterology*, vol. 105, pp. 1643–1650, 1993.

Ling, W.H. et al., "Enzyme Profile of Lactobacillus Strain GG by a Rapid API ZYM System: A Comparison of Intestinal Bacterial Strains" *Microbial Ecology in Health and Disease*, vol. 7, pp. 99–104, 1994.

Majamaa, H. et al., "Lactic Acid Bacteria in the Treatment of Acute Rotavirus Gastroenteritis" *Journal of Pediatric Gastroenterology and Nutrition*, vol. 20, pp. 333–338, 1995.

Meurman, J.H. et al., "Recovery of Lactobacillus Strain GG (ATCC 53103) from Saliva of Healthy Volunteers after Consumption of Yoghurt Prepared with the Bacterium" *Microbial Ecology in Health and Disease*, vol. 7, pp. 295–298, 1994.

Gorbach, S.L., "Lactic Acid Bacteria and Human Health" *Annals of Medicine*, vol. 22; pp. 37–41, 1990.

Isolauri, E., et al., "A Human Lactobacillus Strain (*Lactobacillus Casei* sp strain GG) Promotes Recovery From Acute Diarrhea in Children" *Pediatrics*, vol. 88, pp. 90–97, 1991.

(List continued on next page.)

*Primary Examiner*—Thurman K. Page
*Assistant Examiner*—William E. Benston, Jr.
*Attorney, Agent, or Firm*—Foley, Hoag & Eliot; Beth E. Arnold; Anita Varma

[57] ABSTRACT

Methods for treating or preventing diseases or conditions, which are associated with or caused or contributed to by an opportunistic or pathogenic microorganism in a subject, comprising administering to the subject an effective amount of a culture of lactic acid fermentation microorganisms of the species *Lactobacillus acidophilus* are disclosed.

12 Claims, No Drawings

OTHER PUBLICATIONS

Oksanen, P.J. et al., "Prevention of Travellers' Diarrhoea by Lactobacillus GG" *Annals of Medicine,* vol. 22, pp. 53–56, 1990.

Raza, S. et al., "Lactobacillus GG promotes recovery from acute nonbloody diarrhea in Pakistan" *The Pediatric Infectious Disease Journal,* vol. 14, pp. 107–111, 1995.

Ling, W.H. et al., "Colonization and Fecal Enzyme Activities after Oral Lactobacillus GG Administration in Elderly Nursing Home Residents" *Annals of Nutrition and Metabolism,* vol. 36, pp. 162–166, 1992.

Sepp, E. et al., "Effect of Administration of *Lactobacillus casei* Strain GG on the Gastrointestinal Microbiota of Newborns" *Microbial Ecology in Health and Disease,* vol. 6, pp. 309–314, 1993.

Siitonen, S. et al., "Effect of Lactobacillus GG Yoghurt in Prevention of Antibiotic Associated Diarrhoea" *Annals of Medicine,* vol. 22, pp. 57–59, 1990.

Stansbridge, E.M. et al., "Effects of feeding premature infants with Lactobacillus GG on gut fermentation" *Archives of Disease in Childhood,* vol. 69, pp. 488–492, 1993.

Saxelin, M. et al., "Dose Response Colonisation of Faeces after Oral Administration of *Lactobacillus casei* Strain GG" *Microbial Ecology in Health and Disease,* vol. 4, pp. 209–214, 1991.

Saxelin, M. et al., "Dose Response on the Faecal Colonisation of Lactobacillus Strain GG Administered in Two Different Formulations" *Microbial Ecology in Health and Disease,* vol. 6, pp. 119–122, 1993.

Saxelin, M. et al., "Fecal recovery following oral administration of Lactobacillus Strain GG (ATCC 53103) in gelatine capsules to healthy volunteers" *International Journal of Food Microbiology,* vol. 25, pp. 199–203, 1995.

Millar, M.R. et al., "Eternal feeding of premature infants with :Lactobacillus GG" *Archives of Disease in Childhood,* vol. 69, pp. 483–487, 1993.

Marteau, P. and Rambaud, J. "Potential of using lactic acid bacteria for therapy and immunomodulation in man" *FEMS Microbiology Reviews,* vol. 12, pp. 207–220, 1993.

Salminen, S. and Deighton, M., "Lactic–Acid Bacteria in the Gut in Normal and Disordered States" *Dig Dis,* vol. 10, pp. 227–238, 1992.

Donohue, D.C. et al., "Toxicity of Lactic Acid Bacteria" in *Lactic Acid Bacteria,* Ed. Salminen and von Wright, Marcel Dekker, Inc. New York, Basel, Hong Kong, 1993;I.

Korhonen, H., "Bioactive Compounds in Fermented Milks" *IDF Nutrition Newsletter,* No. 3, pp. 10–11, 1994.

Mikelsaar, M., "Lactobacillar Probiotics and Intestinal Microecology" *IDF Nutrition Newsletter,* No. 3, pp. 11–12, 1994.

Salminen, S. and Tanaka, R., "Role of Cultured and Culture–Containing Dairy Products in Health" *IDF Nutrition Newsletter,* No. 3, pp. 12–15, 1994.

Renner, E., "Role of Cultured and Culture–Containing Dairy Products in Health" *IDF Nutrition Newsletter,* No. 2, pp. 11–14, 1993.

Schaafsma, G., "Lactose Intolerance and Consumption of Cultured Dairy Products—A Review" *IF Nutrition Newsletter,* No. 2, pp. 15–16, 1993.

Nanji, A.A. et al., "Lactobacillus Feeding Reduces Endotoxemia and Severity of Experimental Alcoholic Liver (Disease) (43703)" *P.S.E.B.M.,* vol. 205, pp. 243–247, 1994.

Salovaara, H. et al., "Oat Bran as a Substrate for Lactic Acid Bacteria and Bifidobacteria" *Proceedings of EuroFood Chem VII,* pp. 314–317, 1993.

Salminen, S., "Healthful properties of Lactobacillus GG" *Dairy Industries International,* pp. 236–238, 1994.

Hosoda, Masataka, et al., "Effects of Lactobacillus GG Strain Intake on Fecal Microflora and Defecation in Healthy Volunteers," *Japan Bifidis Foundation,* 8, pp. 21–28, 1994.

Ling, W.H., et al., "Lactobacillus Strain GG Supplementation Decreases Colonic Hydrolytic and Reductive Enzyme Activities in Healthy Female Adults," *J. Nutr.,* 124, pp 18–23, 1994.

Salminen, S., et al., "Lactobacillus GG (Gefilac™) Fermented Whey Drink And Yoghurt," *Scandi Dairy Inf.,* 3, pp. 66–67, 1991.

International Search Report in PCT/RU93/00220, mailed: Jan. 12, 1994.

FERMENTED MILK NUTRACEUTICALS

This application is a Continuation Ser. No. 08/511,875 filed Aug. 4, 1995 now (pending)

BACKGROUND OF THE INVENTION

Fermented Milk Products

A pleasant taste and easy digestibility are common characteristics of fermented milk products. These products are typically nutritious and some have been shown to have medicinal benefit in treating and preventing infectious disease. Fermented milk products can vary not only by the milk, but also by the method of preparation, organoleptic properties, chemical composition and content of microflora.

So-called lactic acid bacteria alone or in symbioses (species or strains of species) and often with yeasts can induce lactic acid fermentation. *Lactobacillus acidophilus* strains are preferred for generating fermented milk products, since these strains are known to remain in the large intestine of humans where they produce anti-microbial substances. Fermented milk products prepared using *Lactobacillus acidophilus* strains are nutritious as well as therapeutic. In addition to anti-microbial benefits, some milk products have been reported to stimulate gastric secretion and motor-secretory function of the entire gastrointestinal tract, reduce serum cholesterol and treat and prevent diarrhea.

Typically, *Lactobacillus acidophilus* fermented milk products include about $10^7$–$10^8$ bacteria per 1.0 g of product and comprise about 2.8 wt. % of protein, 3.5 wt. % of fats, 88.5 wt. % of water, 1173 mg of essential amino acids in 1.0 liter (at a scaling factor of 6.38)[namely valine (157), isoleucine (156), leucine (267), lysine (215), methionine (71), threonine (126), tryptophan (41), phenylalanine (140)], and non-essential amino acids [namely alanine (80), arginine (100), aspartic acid (179), histidine (74), glycine (38), glutamic acid (492), proline (248), serine (153), tyrosine (151), cystine (20)].

A fermented milk product produced by sterilizing milk at 120° C., cooling the milk to 30–34° C. and then introducing from about 0.2 to 0.4 wt. % (milk) of *Lactobacillus acidophilus* strains NK1, KEW24 and 100AW taken in a 2:2:1 ratio, respectively, has been described (Russian Federation Patent SU, A, 1004471). Culturing was carried out at 30–34° C. for 18–24 hours to ferment the milk up to a 180–210 Th acidity (i.e. 1.62–1.89% lactic acid). The fermented milk produced was characterized as having an antagonistic activity against *Shigellae sonnei*, 99.9%; *Shigella flexneri*, 100%; Salmonellae, 99.3%; Proteus sp., 99.9%; and possessing a proteolytic activity of 62.5%. The product was found to be resistant to antibiotics (e.g. monocyclin, neomycin, kanamycin, polymixin, penicillin, erythromycin, streptomycin and tetracyclin). Moreover, the product was reported to possess a resistance to drying over the range of 45–58% viable cells on freeze-drying, a storage stability over the range of 80–90% viable cells-(in the dry form) at room temperature. However, the product has shown no benefits in treating gastrointestinal disease, premature infants or other conditions.

Fermented milk products have also been made by culturing the *L. acidophilus* K1, K5 or K10 strains ($10^7$ to $10^8$ bacteria per gram), which are phenol-resistant, possess an increased antibiotic activity with respect to bacteria of the *Escherichia coli* group including pathogenic microorganisms, with cow milk, seed oil and refined sugar. Their beneficial effect in the digestive tract of infants has been described. ("Producing Child's Milk Products", Moscow, Light and Food Industry, 1982, p. 67.)

A fermented milk product prepared with these strains has been reported to contain the following: protein, 1.8–1.9 wt. %; fat, 3.5 wt. %; carbohydrates, 7.0 wt. %; mineral substances, 0.5 wt. %; water, 87.1–87.2 wt. %. The content (wt. %) of essential amino acids in the fermented milk protein, which result from partial proteolysis of proteins during culturing, was reported to be as follows: lysine, 7.0; threonine, 2.6; methionine, 09; valine, 5.5; phenylalanine, 4.4; leucine, 14.8; isoleucine, 3.2; histidine, 2.5; tryptophan, 2.1. The product is further reported to have an acidity of about 50–70 Th (from $10^7$–$10^8$) and an energy value of about 65 kilocalories per 100 grams of product ("Using Acidophilic Mixtures for Feeding Healthy and Sick Infants of the 1st Year of Life", Moscow, 1980, p. 4–7).

Although the fermented milk product contains protein, fatty acids, carbohydrates, vitamins and minerals, all of which positively influence intestinal biocenosis and can stimulate the immune system, the microorganisms do not produce vitamins. The following artificially supplied vitamins comprise the fermented milk product described above: (vitamins, wt. %) A-0.06; $D_2$-0.01; E-10.0; C-5.0; $B_1$-0.05; $B_2$-0.07; $B_6$-0.04; PP (biotin)-0.4.

*Lactobacillus acidophilus*

*Lactobacillus acidophilus* are microaerobic, Gram-positive, homofermentative, and immobile. They are granular and non-granular asporogenic bacteria of 2–10×0.7–0.8 μm in size. Cells are disposed singly, in short or long chains, and are characterized in that they do not reduce indole and do not form skatole nor dilute gelatine. In addition, *L. acidophilus* does not possess a hemolytic activity. However the bacteria do ferment the following: lactose, glucose, sucrose, fructose, mannose, galactose, maltose, raffinose, starch, dextrin, sorbitol, mannitol, dulcitol, but not inositol on selective agar nutrient media in Burri tubes or Petri dishes. They form subsurface colonies which are shallow, rarely smooth (S-forms), most commonly in the form of a ball of entangled threads (R-forms). The minimal growth temperature is at least 20° C. and preferably 35–39° C. Temperatures of above about 68–70° C. are typically lethal. When cultured in milk, *L. acidophilus* strains result in a maximum acidification of about 300–360 Th, a phenol resistance of about 0.9–1.0%, a 0.9–1.0%, and a synthomycin resistance of about 0.003%.

A. Er-2 strains

Some *L. acidophilus* bacteria, the Er-2 group, are known flavin producers. Examples of Er-2 strains include Nos.: 317/381, 317/393, 317/401 or 317/389 (L. A. Erzinkyan; Biological Features of Some Lactic Acid Bacteria Strains, Academy of Armenian Sciences Publishers, Yerevan, 1971, pp. 79–96, 172). In addition, Er-2 strains of *Lactobacillus acidophilus* are known to produce a substantial amount of antimicrobial substances which are beneficial for humans. These substances have been shown to suppress growth and development of Gram-positive (e.g. *Staphylococcus aureus*) and Gram-negative (e.g. *Escherichia coli*) bacteria including, without exception, all dysentery and dysentery-like diseases induced by bacteria.

B. *Lactobacillus acidophilus* N.V 317/402

Fermented milk products, which possess high dietary versatility, easy assimilability, curative properties, and a high nutritive value have been obtained using *Lactobacillus acidophilus* strain N.V. Er 317/402 (Nauka Industry Co. Ltd., Japan). When preparing a fermented milk product, 1.0 wt. % of this strain is introduced into whole milk at 28–40° C., wherein milk clotting occurs within 5–8 hours (Russian Federation Patent No. SU, A, 1635573). The strain used possesses a slow acid-forming capability. A maximum acidification value reaches about 360 Th.

Bacteria of this strain are capable of producing a substantial amount of antibiotics, which are harmless and in fact beneficial for humans (particularly infants). These antibiotics suppress growth and development of both Gram-positive and Gram-negative bacteria including all bacterial inducers of active forms of gastronomical diseases. The presence of the strains in vitro have resulted in growth suppression zones for the following organisms: *Staphylococcus aureus* (30–35 mm), *Escherichia coli* (20–25 mm), *Salmonella typhimurium* (20–23mm) and klebsiella (20–22). thirty-six years of investigations have shown absence of phagolysis (i.e. destruction of leukocytes necessary in wound healing and inflammation control) with this strain.

*Lactobacillus acidophilus* N.V. 317/402 was produced in 1949 by a directed selection in Yerevan (The Armenian Republic). A stock culture was isolated from the feces of healthy newborns. The bacteria can be inoculated into a liquid nutrient medium and stored at 5–8° C. Alternatively, the culture can be lyophilized (freeze-dried) and stored at 5–8° C. The strain can also be stored in liquid nitrogen at −193 C. *Lactobacillus acidophilus* N.V. 317/402 are facultative anaerobes. To maintain the strain, the culture should be reinoculated once every 1–1.5 months. Milk is the preferred medium for propagating the culture.

The strain has been characterized as being homofermentative, immobile, Gram-positive, microaerophilic, asporogenic bacilli of about 2–20×0.8–0.9 μm in size. Cells are disposed singly or in the form of short chains. Subsurface shallow colonies form on selective agar media, most commonly as balls or in the form of mixed up threads (R-forms). The strain does not reduce nitrates, form skatole or indole, dilute gelatine, nor possess a hemolytic activity. It does ferment the following: lactose, glucose, sucrose, fructose, mannose, galactose, maltose, raffinose, starch, dextrin, sorbitol, mannitol, and dulcitol, but does not ferment inositol. In milk the strain results in a phenol resistance of about 0.9–1.0% and a synthomycin resistance of about 0.003%.

*Lactobacillus salivarius*

Bacteria of this species are Gram-positive, homofermentative, immobile, granular and non-granular asporogenic. Cells are disposed singly, in short or long chains, they do not reduce nitrates and do not form indole or skatole, nor dilute gelatine. The bacteria do not possess hemolytic activity. They do ferment the following: galactose, lactose, maltose, mannitol, sucrose, esculin, melibiose, raffinose, rhamnose, sorbitol. A limiting acid formation is 230–260 T. They do not form gas from glucose, and do not grow at 15 C. An optimal culturing temperature is about 39 or 40° C. *Lactobacillus salivarius* subsp. *salicinius* strain 11742 and *Lactobacillius salivarius* subsp. *salivarius* strain 11741 are available from the American Type Culture Collection.

SUMMARY OF THE INVENTION

In one aspect, the invention features bacterial cultures or ferments that can be cultured in milk. In one embodiment, the ferment comprises *Lactobacillus acidophilus* strain N.V. Er 317/402 and at least one strain from the group Er-2, preferably in a ratio of 1–4:1, respectively. In another embodiment, the ferment comprises *Lactobacillus acidophilus* strain N.V. Er 317/402 and at least one strain from the group Er-2, preferably in a ratio of 1–4:1, respectively and further comprises a *Lactobacillus salivarius* in a 1:1 ratio with the total *Lactobacillus acidophilus* content.

In another aspect, the invention features fermented milk products produced by culturing milk with an appropriate amount of the novel ferments. In one embodiment, the fermented milk product is a liquid (e.g.a fermented milk drink or infant formula). In another embodiment, the milk product is solidified (e.g. into a yogurt, curd or ice cream-like composition). In a further embodiment, the fermented milk product is a powder, that can be reconstituted, for example, into a liquid or solidified milk product or prepared into a pharmaceutical composition (e.g. an orally administrable capsule, suppository or topical ointment).

The above and other features of the invention will now be more particularly described and pointed out in the following Detailed Description and Claims.

DETAILED DESCRIPTION OF THE INVENTION

The invention features biologically active fermented milk products prepared using novel cultures of lactic acid bacteria of the species *Lactobacillus acidophilus*. The resulting products possess nutritive, prophylactic and therapeutic properties.

The novel culture or ferment comprises a combination of known *Lactobacillus acidophilus* strain of the group Er-2 and the known strain *Lactobacillus acidophilus* N.V. Er 317/402. Example of strains of the Er-2 group of *Lactobacillus acidophilus* include: 317/381, 317/393, 317/401 and 317/389. A preferred ferment is comprised of *Lactobacillus acidophilus* strain N.V. Er 317/402 and at least one strain from the Er-2 group of Lactobacillus, preferably in a ratio of 1–4:1 with the strain of The antibiotic activity of the culture, particularly against organisms found in the intestines of humans and non-human animals, can be further increased by combining a *Lactobacillus salivarius* strain with the novel culture described above. Preferred *Lactobacillus salivarius* strains include strain numbers 1588, 11741, 11742 and 29602. Preferably the *Lactobacillus salivarius* strain is in a 1:1 ratio with the total content of *Lactobacillus acidophilus*.

Fermented milk products produced in accordance with the present invention, may be prepared from virtually any milk obtained from any source (e.g., cow, goat, sheep, mare, buffalo, human etc.) and of any composition (e.g whole, low-fat, fat-free, cream or otherwise modified). In addition, A variety of "additives" can be included either before, after or while the milk is being cultured. Examples include color (e.g., beta-carotene, anatto, tumeric, paprika and FD & C dyes); flavors, aromas or sweeteners (e.g., fructose, sucrose, glucose, mannose, levulose, galactose, maltose, raffinose, melibiose, starch, dextrin, sorbitol, mannitol, dulcitol, inositol, aspartame, honey, vanillin, chocolate, orange, cherry, peach, strawberry, pineapple, raspberry, guava, mango, banana, blueberry; emulsifiers &/or thickening agents (e.g., phosphatides such as egg yolk, soybean or corn lecithin or substances such as mono- or di- glycerides, gum arabic, tragacanth, arabinogalactan, carrageenan, furcellaran, sodium alginate, bean gum, gum xanthan, guar gum, and apple pectin); preservatives, vitamins and antioxidants (e.g., vitamins A, C, D, E, B-1, B-5, B-6, zinc, selenium, calcium, alpha-tocopherol, glutathione, butylated hydroxytoluene (BHT), butylated hydroxyanisole (BHA), and cysteine).

Preferably, the fermented milk products are prepared by introducing an appropriate amount of the novel culture into pasteurized milk and allowing fermentation to proceed at an appropriate temperature and for an appropriate period of time to obtain a product of suitable acidity. Preferably the acidity of a food product is in the range of about 60–165 Th (0.5400–1.4850% lactic acid). However for use as a pharmaceutical, as described below, the fermented milk product can have an acidity up to about 270–280 Th (0.5400–2.2600% lactic acid) and contain about $10^6$–$10^9$ culture bacteria per gram of product. An appropriate fermenting temperature is a temperature that accomodates the metabolism of the culture organisms. Optimal temperatures for culturing *Lactobacillus acidophilus* strains range from about 20° C. to about 50° C.

If the milk to be fermented has not been pasteurized, sterilization can be accomplished using methods which are well-known in the art. For example, the milk can be heat-treated at an appropriate temperature, which can vary according to the type of milk, the ultimate manufactured product and the needs of the consumer. Many years of monitoring the production of the product described herein by constant quality indices, (e.g., acidity, amino acid composition and vitamin content) have shown consistent and stable manufacture and storage.

The resulting fermented milk products are highly nutritious. The products have typical energy values of about 20 to about 540 kilocalories (per 100 gms of product). In addition, they are typically comprised of the following (wt. %): proteins, 0.35–34.0; fats, 0.05–36.0; carbohydrates, 1.5–70.0; organic acids (in terms of lactic acid), 0.6–56.0 wt.; vitamins (in 100 grams), 0.95–15.9 mg; water, 3.7–94.6 wt. The protein component of the product is typically comprised of the following essential amino acids (in percent based on the sum of amino acids in the product): valine, (10.4–10.77); isoleucine, (9.6–9.7); leucine (13.8–14.1); lysine (3.6–5.0); methionine (2.7–3.1); threonine (0.9–1.1); tryptophan (0.5–0.7); phenylalanine (8.4–8.5).

Additionally, the fermented milk products typically contain the following vitamins (per 100 gms of product): Vitamin A, traces-0.05 mg; Pantothenic acid, 0.10–0.19 mg; Vitamin C, 0.5–0.90 mg; Biotin, 0.002 mg; Vitamin E (tocopherol), traces-0.2 mg; Nicotinic acid, 0.040–0.047 mg; Niacin, 0.09–0.14 mg. Vitamins of the group B, 0.218–0.315 mg, including: Vitamin B1 (thiamin), 0.04–0.07 mg; Vitamin B2 (riboflavin), 0.15–0.20 mg; Vitamin B6 (pyridoxine), 0.025–0.04 mg; folic acid, 0.003–0.005 mg. In fact, milk fermented with the novel cultures have been found to have enhanced vitamin content particularly with regard to group B vitamins, vitamin C, pantothenic acid, biotin, vitamin E, nicotinic acid, and niacin.

In addition to being nutritious, fermented milk products containing the novel cultures of microorganisms are active antagonists of opportunistic and pathogenic microorganisms and therefore their presence in vivo is beneficial for treating diseases or conditions that are caused by or contributed to by opportunistic or pathogenic microorganisms. Examples include gastrointestinal diseases such as dysbacteriosis, salmonellosis, constipation, colitis, lactose intolerance, dysentery and common diarrheas, (resulting for example from infection by microorganisms such as *Escherichia coli*, Enterobacter sp. Salmonella sp. and Proteus sp.), hemolytic jaundice (resulting for example from infections by microorganisms such as *Staphylococcus aureus*, Klebsiella sp. and *Pseudomonas aeruginosa*), omphalitis in newborns, in obstetric-and-gynecological practice (e.g. treating vulvovaginitis), other pyo-inflanmnatory diseases; for treating urethritis, bladder infections, allergies, sinusitis, rhinitis, high serum cholesterol, blood, liver, kidney diseases, atrophy and dystrophy with children, sepsis, certain cancers (e.g. colon, colo-rectal and breast), and infected wounds. As studies reported in the following Examples have shown, fermented milk products containing the claimed symbiotic microorganisms are inducers of α- and γ-interferons and therefore enhancement of a subject's (e.g. human's or animal's) immune response.

Since the cultures are well adapted to the gastrointestinal tract of humans and animals and eliminate disease causing organisms therein, administration of the cultures is particularly useful for treating or preventing intestinal dysbacteriosis (i.e. a change to the indigenous microbial flora in a human or animal resulting from the presence of antibiotics, chemotherapeutics or infectious organisms (e.g. Salmonella sp.)) Further, the cultures have been found to be resistant to high phenol concentrations, and certain toxic chemicals, chemotherapeutics, and antibiotics and therefore is thought to remain in a subject's gastrointestinal tract for a period of time after initial introduction.

The fermented milk product can be prepared as a liquid (e.g.a fermented milk drink or infant formula). To prepare fermented milk products suited for feeding and treating premature and other children of all ages, the product resulting from culturing can be subjected to separation under aseptic conditions to give a liquid fraction of the following composition: proteins, 0.35–0.8 wt. %; fats, 0.05–0.20 wt. %; carbohydrates, 1.5–3.8 wt. %; organic acids (in terms of lactic acid), 0.70–3.15 wt. %; vitamins, 1.18–1.54 mg/100 g; water, 3.7–94.6 wt. %. The protein fraction remaining upon separation of the liquid fraction generally has the following composition: proteins, 5.5–11.0 wt. %; fats, 0.1–6.0 wt. %; carbohydrates, 1.6–2.0 wt. %; organic acids (in terms of lactic acid), 1.0–2.0 wt. %; vitamins, 1.2–1.56 mg/100 g; water, 83.4–86.6 wt. %. Alternatively, the milk product can be thickened into a semi-solid or solid composition (e.g. a yogurt, butter, cheese or ice cream-like composition).

Further, the fermented milk product can be prepared as a powder (e.g. by freeze drying). Experiments have shown that a powder prepared from a fermented milk product as disclosed herein can be stored for prolonged periods and can be readily reconstituted, for example, into a liquid or solidified milk product. A preferred fermented milk powder contains: proteins, 6.0–12.9 wt. %; fats, 0.9–3.3 wt. %; carbohydrates, 26.7–70.2 wt. %; organic acids (in terms of lactic acid), 15.4–56.0 wt. %; vitamins (per 100 grams of the product), 11.8–15.4 wt. % and water, 4.0 wt. %. A particularly preferred powder is obtained by freeze drying a fermented milk product, which has a 60–280° Th (0.5400–0.5600 lactic acid) acidity to a water content of not more than 4 wt. %. The powder can be reconstituted to prepare a liquid (e.g. baby food formula or fermented milk drink) or thickened into a semi-solid or solid composition.

In view of their recognized medicinal value, the fermented milk powder or lyophilized culture can be formulated into pharmaceutical compositions (e.g. a capsule, suppository or ointment) for enteral or topical administration. In order to obtain a concentrated product suitable for medical use, in vitro and in vivo fermentation can be carried out up to an acidity of about 270–280° Th.

A preferred pharmaceutical is prepared from the liquid fraction obtained after fermentation and which has been separated under aseptic conditions is subjected to freeze drying up to a humidity of not more than about 4 wt. % to prepare a powdered substance comprising the following: proteins, 7.7–12.9 wt. %; fats, 0.8–3.3 wt. %; carbohydrates, 26.7–70.2 wt. %; organic acids (in terms of lactic acid), 15.4–56.0 wt. %; vitamins (in 100 grams), 11.80–15.4 mg; water, 4.0 wt. %. Storage of the product, even under elevated temperatures has been found not to alter the biochemical properties.

A pharmaceutical composition comprising the fermented milk product can be enterally administered to a subject (e.g human or animal) alone, or in conjunction with a pharmaceutically acceptable carrier. As used herein, the phrase "pharmaceutically acceptable carrier" is intended to include substances that can be coadministered with an appropriate fermented milk product and allows the invention to perform its intended function. Examples of such carriers include solutions, solvents, dispersion media, delay agents, emulsions and the like. The use of such media for pharmaceutically active substances are well known in the art. Any other conventional carrier suitable for use with the invention also falls within the scope of the present invention.

Alternatively, pharmaceutical compositions, which have been prepared as ointments, tinctures, creams, gels, solutions, lotions, sprays, suspensions and suppositories can be topically administered.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE

Example 1
Ferment Obtained By Inoculating Milk with a 1:2 Culture of Er-2 *Lactobacillus acidophilus* Strains 317/392, 317/395, 317/396 and *Lactobacillus acidophilus* Strain N.V. Er 317/402

Ten kg of a fat-free cow milk was sterilized at 120 C for 20 minutes, cooled to 40° C., then inoculated with 240 grams symbiotic microorganisms consisting of 80 grams each of the strains 317/392, 317/395, 317/396 of the group Er-2 *Lactobacillus acidophilus* taken in equal amounts, and 160 grams of the strain N.V. Er 317/402 of *Lactobacillus acidophilus*. The microorganisms were thoroughly mixed with the milk and allowed to stand for 47 hours. The fermented product obtained was cooled to 8° C. and again allowed to stand for 12 hours. The acidity of the liquid product was 280 T. The liquid product was found to mainly consist of: water, 91.8 wt. %; total solids, 8.2 wt. %, including: proteins, 2.8 wt. %; fats, 0.1 wt. %; carbohydrates, 1.5 wt. %; organic acids and other fermentation products, 3.1 wt. %; ash, 0.7 wt. %. The following minerals were contained in 100 grams of the product: sodium, 52 mg; potassium, 146 mg; calcium, 121 mg; magnesium, 14 mg; phosphorus, 90 mg; iron, 0.1 mg; vitamins, 1.530 mg. The product was determined to have an energy value of about 29.2 kilocalories per 100 grams.

Example 2
Freeze-Dried Fermented Milk Product

A fermented milk product prepared as described in Example 1 was subjected to freeze drying at an initial temperature of —50° C., a final temperature of about –26 C and a residual pressure of $13.3 \times 10^3$ Pa for 24 hours. The product was reconstituted to a 3.7 wt. % water content and 96.3 wt. % dry weight consisting mainly of: proteins, 32.8 wt. %; fats, 1.1 wt. %; carbohydrates, 20.8 wt.%; organic acids, 36.4 wt. %; ash, 5.2 wt. %; vitamins 15.40 mg/100 grams. The following minerals were contained in 100 grams of the reconstituted product: sodium, 501 mg; potassium, 1,352 mg; calcium, 1,120 mg; magnesium, 51 mg; phosphorus, 630 mg; iron, 1 mg. The product was determined to have an energy value of 29.2 kilocalories per 100 grams. The content of microorganisms was determined to be about $3 \times 10^9$ per gram of product.

Example 3
Ferment Obtained By Inoculating Milk with a 1:1 Culture of Er-2 *Lactobacillus acidophilus* Strain 317/392 and *Lactobacillus acidophilus* Strain N.V. Er 317/402

Ten kg of a fat-free cow milk was sterilized at 121 C for 19 minutes, cooled to 37° C., then 200 grams of symbiotic microorganisms consisting of 100 grams of the strain 317/392 of the group Er-2 *Lactobacillus acidophilus* and 100 grams of the strain N.V. Er 317/402 of *Lactobacillus acidophilus* were introduced. Symbiotic microorganisms were thoroughly mixed with the fat-free milk and allowed to stand at 37 C for five hours. The ferment obtained was cooled to 6 C and again allowed to stand for 12 hours. The product was determined to have an acidity of 76° T.

The fermented milk product was mainly comprised of. water, 91.5 wt. %; dry substances, 8.5 wt. %; including, proteins, 3.0 wt. %; fats, 0.05 wt. %; carbohydrates, 4.1 wt. %; organic acids, 0.65 wt. %; ash, 0.7 wt. %. 100 grams of the product was found to include the following minerals: sodium, 50 mg; potassium, 146 mg; calcium, 121 mg; magnesium, 14 mg; phosphorus, 90 mg; iron, 0.1 mg; vitamins, 1,950 mg. The product was determined to have an energy value of 31.2 kilocalories per 100 grams.

Example 4:
Whole Milk Infant Formula

The following were added together: 522 kg of whole milk (3.2% fats; 3.0% proteins; 4.7% carbohydrates), 6.23 kg of a refined olive oil (premixed homogenously with 63 kg of cream), 42.2 kg of carbohydrates, 45 kg of dextran-maltose (containing 60 wt. % of carbohydrates) and 15.2 kg of sugar. The mixture obtained was sterilized at 136° C., and cooled to 36° C. Twenty kg of the fermented milk product prepared as in Example 3 was added to a cooled mixture and allowed to stand at this temperature for 5.5 hours, thereupon the mixture was quickly cooled to 6° C. and allowed to stand for 12 hours. A homogeneous product with a smooth consistency, a sweet fermented taste and a 67° Th (0.6075% lactic acid) acidity was obtained.

The main components of the fermented milk product was as follows: water, 87.05 wt. %; total solids, 12.95 wt. %; including: proteins, 1.8 wt. %; fats, 3.5 wt. %; carbohydrates. 6.4 wt. %; organic acids, 0.6 wt. %. Mineral substances per 100 grams of the product: sodium, 21 mg; potassium, 95 mg; calcium, 82 mg; magnesium, 7 mg; phosphorus, 50 mg; iron, 0.1 mg, vitamins, 1.23 mg. The energy value was calculated to be about 66.5 kilocalories per 100 grams. One gram of the product was estimated to contain about $4 \times 10^8$ *Lactobacillus acidophilus*. In view of its nutritive and immunostimulatory properties, the product can be used as an infant formula in place of breast milk.

Example 5
Ferment Obtained By Inoculating Milk with a Culture of Er-2 *Lactobacillus acidophilus* Strains 317/392, 317/395, 317/396, *Lactobacillus acidophilus* Strain N.V. Er 317/402 and *Lactobacillus salivarius*, Strain No. 1588

One thousand kg of a cow milk (3.5 wt. % fat and 3.0 wt. % of protein) was purified, heat-treated at 95 C, allowed to stand for 15 minutes and cooled to 39 C. Then 30.0 kg of symbiotic microorganisms consisting of 15.0 kg of microorganisms of *Lactobacillus acidophilus* (5.0 kg of the strains 317/392, 317/395, 317/396 of the group Er-2 and 10.0 kg of the strain N.V. Er 317/402) and 15.0 kg of microorganisms of *Lactobacillus salivarius*, strain No. 1588, were introduced. Symbiotic microorganisms were thoroughly mixed with the milk and allowed to stand at 39° C. for 3.5 hours. The fermented product obtained was cooled to 7° C. and again allowed to stand for 13 hours. The acidity of the finished fermented milk product was estimated to be about 155° Th (1.3950% lactic acid).

The main components of the fermented milk product were as follows: water, 88.1 wt. %; total solids, 11.9 wt. %, including: proteins, 3.0 wt. %; fats, 3.5 wt. %; carbohydrates, 3.7 wt. %; organic acids, 1.0 wt. %; mineral substances in 100 grams of the product: sodium, 50 mg; potassium, 146 mg; calcium, 121 mg; magnesium, 14 mg; phosphorus, 90 mg; iron, 0.1 mg; vitamins, 1.59 mg. An energy value is 62.0 kilocalories per 100 grams. The number of microorganisms was estimated to be about $5 \times 10^9$ per gram of product.

Example 6
Ferment Obtained By Inoculating Milk with a 1: 1 Culture of Er-2 *Lactobacillus acidophilus* Strain 317/395 and *Lactobacillus acidophilus* Strain N.V. Er 317/402

Ten kg of a fat-free cow milk was sterilized at 120° C. for 20 minutes, cooled to a 36° C. temperature, then 200 grams of symbiotic microorganisms consisting of 100 grams of the strain 317/395 of the group Er-2 *Lactobacillus acidophilus* and 100 grams of the strain N.V. Er 317/402 of *Lactobacillus acidophilus* were introduced. The bacteria were thoroughly mixed with the milk and allowed to stand for 5.5 hours. The fermented product obtained was cooled to 6° C. and again allowed to stand for 12 hours. The acidity of the liquid product was estimated to be about 90° Th (0.8100% lactic acid).

The product was found to mainly consist of: water, 91.5 wt. %; total solids, 8.5 wt. %, including: proteins, 3.0 wt. %; fats, 0.1 wt. %; carbohydrates, 3.9 wt. %; organic acids, 0.7 wt. %. 100 grams of the product contained 1.097 mg of vitamins and the following minerals: sodium, 52 mg; potassium, 152 mg; calcium, 126 mg, magnesium, 14 mg; phosphorus, 95 mg; iron, 0,1 mg. The number of microorganisms in one gram of product was determined to be about is $5 \times 10^8$.

Example 7
Low-Fat Infant Formula

Ten kg of milk having a 2 wt. % fat content and 3.0 wt. % protein content was sterilized at 121° C. for 20 minutes then cooled to 38° C. 200 grams of symbiotic microorganisms consisting of 50 grams of *Lactobacillus acidophilus* group Er-2 strain 317/396 and 150 grams of the *Lactobacillus acidophilus* strain N.V. Er 317/402 were introduced and thoroughly mixed with the milk, which was then allowed to stand for 4.5 hours. The fermented product obtained was then cooled to 8° C. and again allowed to stand for 12 hours. The acidity of the product obtained was determined to be 90° T. The product was then separated under aseptic conditions into liquid and curd fractions.

The liquid fraction was found to be comprised of: water (94.6 wt. %) and total solids 5.4 wt. %; including: proteins, 0.35 wt. %; fats, 0.05 wt. %; carbohydrates, 3.7 wt. %; organic acids, 0.8 wt. %, ashes, 0.5 wt. %. The following minerals were determined to be contained in 100 grams of the liquid fraction: sodium, 41 mg; potassium, 125 mg; calcium 60 mg; magnesium, 6 mg; phosphorus, 71 mg; iron, 0.1 mg; vitamins, 1.18 mg. The product was determined to have an energy value of 19.6 kilocalories/100 grams. The number of microorganisms contained in the liquid fraction was determined to be $6 \times 10^9$ per gram. Based on its nutritional and immune stimulatory properties, the liquid fraction can be used, for example, as a baby food formula.

The curd fraction was found to be comprised of the following: water, 86.6 wt. %; total solids, 13.4 wt. %; including: proteins, 5.5 wt. %; fats, 4.0 wt. %; carbohydrates, 2.0 wt. %; organic acids, 1.0 wt. %, ashes, 0.9 wt. %. The following minerals were determined to be contained in 100 grams of the curd fraction: sodium, 41 mg; potassium, 125 mg; calcium, 146 mg; magnesium, 23 mg; phosphorus, 100 mg; iron, 0.1 mg. An energy value is 19.6 kilocalories/100 grams. 1.32mg of vitamins were contained in 100 grams of the product. The number of microorganisms contained in the protein fraction was determined to be $6 \times 10^6$ per gram. The curd fraction with and without the addition of carbohydrates can be used as a food product (e.g. a fermented milk or yogurt).

Example 8
Powdered Fermented Milk Product

The liquid fraction of the fermented milk prepared under conditions identical to those described in Example 7, was subjected to freeze-drying at an initial temperature of −50° C. and a final temperature of −26° C. and a residual pressure of $13.3 \times 10^3$ Pa for 23 hours. The dried product obtained was found to be stable and unchanged in chemical properties even after being stored for more than two years. The final product consisted of: water, 4.0 wt. %; total solids, 96 wt. %, including: organic acids, 12.6 wt. %; fats, 0.9 wt. %; proteins, 6.3 wt. %; carbohydrates, 70.6 wt. %; ash, 6.0 wt. %. The following minerals were contained in 100 grams of product: sodium, 420 mg; potassium, 1,300 mg; calcium, 600 mg; magnesium, 48 mg; phosphorus, 700 mg; iron, 1.5 mg. An energy value of 359 kilocalories per 100 grams of product was calculated. The number of microorganisms per gram was found to be $3 \times 10^9$. The vitamin content was found to be 11.8mg/100 grams of the product.

Example 9
Medicinal Fermented Milk Product

One thousand kg of cow milk containing 3.5 wt. % of fats and 3.0 wt. % of protein was heat-treated at 95° C., allowed to stand for 20 minutes and cooled to 39° C. 20.0 kg of symbiotic microorganisms consisting of 4 kg of equal amounts of *Lactobacillus acidophilus* strains 317/392, 317/395 and 317/396 of the group Er-2 and 12 kg of microorganisms of the strain N.V. Er 317/402 were introduced into the milk. The microorganisms were thoroughly mixed with the milk and allowed to stand at 38° C. for 4.5 hours. The fermented milk product obtained was cooled to 8 C and again allowed to stand for 16 hours.

The product obtained has an acidity of about 110° T (0.9900% lactic acid) and consisted essentially of: water, 88.1 wt. %; total solids, 11.9 wt. %; including: proteins, 3.0 wt. %; fats, 3.5 wt. %; carbohydrates, 3.80 wt. %; lactic acid, 0.90 wt. %; ash, 0.7 wt. %. The following minerals were contained in 100 grams of the product: sodium, 50 mg; potassium, 146 mg; calcium, 121 mg, magnesium, 14 mg; phosphorus, 80 mg; iron, 0.1 mg; vitamins, 1.54 mg. The number of microorganisms is 600 million in one gram. An energy value is 62.0 kilocalories per 100 grams.

Example 10
Fat-Free Ferment or Dietary Supplement

Ten kg of a fat-free cow milk was sterilized at 121° C. for 19 minutes, cooled to a 40° C. temperature. Into the milk was introduced 400 grams of symbiotic microorganisms consisting of 200 grams of equal parts of microorganisms of the strain 317/401 of the group Er-2 *Lactobacillus acido-*

*philus* and the strain N.V. Er 317/402 of *Lactobacillus acidophilus*, in equal amounts, and 200 grams of microorganisms of *Lactobacillus salivarius* (strain 1588). The mixture was allowed to stand until a fermented gel was obtained, cooled to 6° C. and further allowed to stand for 12 hours.

The final product consisted of: water, 91.75 wt. %; total solids, 8.25 wt. %; including: proteins, 2.8 wt. %; fats, 0.1 wt. %; carbohydrates, 3.75 wt. %; lactic acid, 0.9 wt. %; ash, 0.7 wt. %. 100 grams of the product contained the following minerals: sodium. 50 mg; potassium, 141 mg; calcium, 120 mg; magnesium, 15 mg; phosphorus, 80 mg; iron, 0.1 mg; vitamins, 1.27 mg. The final product has an energy value of 30.3 kilocalories per 100 grams and contains about $7 \times 10^8$ microbes in one gram.

Example 11
Liquid Ferment & Medicinal Agents

Eighty kg of a fat-free milk was sterilized at 120° C. for 20 minutes, cooled to 40° C., then 2.0 kg of the ferment consisting of 0.5 kg of the strain 317/392 of the group Er-2 *Lactobacillus acidophilus* and 1.5 kg of the strain N.V. Er 317/402 of *Lactobacillus acidophilus* was introduced. The ferment was then mixed with the milk and allowed to stand for 4.5 hours. The fermented milk was quickly cooled to 6° C., allowed to stand for 20 hours and then packed into sterile 50 cm³ containers. The acidity of the liquid fermented milk was 160° Th (1.4400% lactic acid).

The final product consisted of: water, 91.9 wt. %; total solids, 8.1 wt. %; including: proteins, 2.8 wt. %; fats, 0.05 wt. %; carbohydrates, 3.6 wt. %; organic acids, 1.0 wt. %; ash, 0.65 wt. %. Vitamin content is 1.33 mg per 100 grams of the product. An energy value is 29.6 kilocalories per 100 grams. Mineral substances in 100 grams are: sodium, 49 mg; potassium, 142 mg; calcium, 125 mg; magnesium, 15 mg; phosphorus, 85 mg; iron, 0.1 mg. A number of microorganisms is $6.0 \times 10^9$ cells in one gram.

Example 12
Powdered Ferment & Medicinal Agents

The product prepared as in Example 11 was subjected to freeze-drying at the initial temperature of −50° C. and final temperature of −26° C. and a residual pressure of $13.3 \times 10^3$ Pa for 24 hours. The final product mainly consisted of: water, 4.0 wt. %; total solids, 96 wt. %; including: proteins, 25.9 wt. %; fats, 0.6 wt. %; carbohydrates, 49.2 wt. %; organic acids, 13.5 wt. %; ash, 6.8 wt. %. The following minerals were contained in 100 grams of the product: sodium, 501 mg; potassium, 1,410 mg; calcium, 1,230 mg; magnesium, 143 mg; phosphorus, 830 mg; iron, 0.5 mg; vitamins, 14.3 mg. The product contained an energy value of 354 kilocalories per 100 grams. $3 \times 10^9$ microorganisms were present in one gram of product. The product obtained can be used as a dry ferment for an industrially manufactured product or as a medicinal agent for oral administration. The obtained product remains unchanged in its properties as a ferment for three months and as a medicinal agent (e.g. powdered ferment) for over two years.

Example 13
Orally Administrable Pharmaceutical Compositions

One thousand kg of a cow milk (3.5 wt. % of fats and 3.0 wt. % of proteins) was filtered, heat treated at 94° C., allowed to stand for 15 minutes and cooled to 40° C. Then 30.0 kg of symbiotic microorganisms consisting of 15.0 kg of microorganisms of *Lactobacillus acidophilus* 317/396 of the group Er-2 and the strain N.V. Er 317/402 taken in a 1:4 ratio, respectively; and 15.0 kg of microorganisms of *Lactobacillus salivarius* (strain 1588) were introduced. The microorganisms were thoroughly mixed with the milk and allowed to stand at 40° C. for 4.0 hours. The fermented product obtained was cooled to 7° C. and again allowed to stand for 14 hours. An acidity of the final product was found to be 165° Th (1.4850% lactic acid).

The final product mainly consisted of: water, 88.0 wt. %; total solids, 12.0 wt. %; including: proteins, 3.1 wt. %; fats, 3.5 wt. %; carbohydrates, 3.7 wt. %; organic acids (in terms of lactic acid), 1.0 wt. %. ash, 0.7 wt. %; wherein in 100 grams of the product, the following elements are contained: sodium, 50 mg; potassium, 146 mg; calcium, 121 mg; magnesium, 14 mg; phosphorus, 90 mg; iron, 0.1 mg; vitamins, 1.59 mg. An energy value of 62.3 kilocalories per 100 grams was determined. The product obtained may be used for oral administration in acute, serious forms of gastrointestinal tract diseases.

Example 14
High-energy, fat-free food and medicine

The fermented milk product, prepared under conditions identical to those described in Example 1, was separated under aseptic conditions into liquid and curd fractions. The liquid fraction was subjected to freeze drying at the initial temperature of −50° C. and an end temperature of −26° C. and a residual pressure of $13.3 \times 10^3$ Pa for 24 hours. The liquid fraction before drying consisted of: water, 94.4 wt. %; total solids, 5.6 wt. %; including: proteins, 0.35 wt. %; fats, 0.05 wt. %; carbohydrates, 1.5 wt. %; organic acids, etc., 3.2 wt. %; ash, 0.5 wt. %. The freeze-dried powder contained: water, 4 wt. %; total solids, 96 wt. %; including: proteins, 6 wt. %; fats, 0.9 wt. %; carbohydrates, 27.0 wt. %, organic acids, 56.0 wt. %, ashes, 6.1 wt. %. The following minerals were contained in 100 grams of the protein fraction: sodium, 510 mg; potassium, 1400 mg; calcium, 1,210 mg; magnesium, 130 mg; phosphorus, 800 mg; iron, 1.0 mg; vitamins, 15.3 mg. An energy value is 298 kilocalories per 100 grams was calculated.

Example 15
Fat-Free Ferment & Medicinal Agent 10 kg of fat-free cow milk was sterilized at 120° C. for 15 minutes, cooled to 36° C., then 200 grams of symbiotic microorganisms consisting of 40.0 grams of the strains 317/392, 317/396 of the group Er-2 *Lactobacillus acidophilus* taken in equal amounts, and 160 grams of microorganisms of the strain N.V. Er 317/402 of *Lactobacillus acidophilus* were introduced into the cooled milk. The microorganisms were thoroughly mixed with the fat-free milk and allowed to stand for 5.5 hours. The fermented product obtained was cooled to 6 C and again allowed to stand for 12 hours.

The liquid fermented milk was determined to have an acidity of about 85 Th (0.7650% lactic acid) and to consist essentially of: water, 91.9 wt. %; total solids, 8.1 wt. %; including: proteins, 2.8 wt. %; fats, 0.1 wt. %; carbohydrates, 3.7 wt. %; organic acids, 0.8 wt. %; ash, 0.7 wt. %. The following elements were contained in 100 grams of the product: sodium, 51 mg; potassium, 144 mg; calcium, 118 mg; magnesium, 15 mg; phosphorus, 90 mg; iron, 0.1 mg. The product's vitamin content was determined to be 1.08 mg per 100 grams of the product. An energy value is 30 kilocalories per 100 grams was determined. The final product was determined to contain about $5 \times 10^8$ microorganisms per gram.

Example 16
Low-Fat Infant Formula

One thousand kg of milk having a fat content of about 2.2 wt. % and containing about 3.0 wt. % of proteins was sterilized at 136° C. for about five seconds, cooled to 38° C., then 15 kg of symbiotic microorganisms consisting of five kg of microorganisms of the strain 317/395 of the group Er-2 *Lactobacillus acidophilus* and 10 kg of microorganisms of the strain N.V. Er 317/402 of *Lactobacillus acidophilus*, were introduced. Symbiotic microorganisms were thoroughly mixed with the milk and allowed to stand at 38° C. for 4 hours. The fermented product obtained was cooled to 6° C. and again allowed to stand for about 18 hours. The resulting product having an acidity of about 120° Th (1.0800% lactic acid) was separated under aseptic conditions into liquid and curd fractions.

The liquid fraction consisted essentially of: water, 93.8 wt. %; total solids, 6.2 wt. %; including. proteins, 0.8 wt. %; fats, 0.2 wt.% carbohydrates, 3.7 wt. %; organic acids, 1.0 wt. %; ash, 0.5 wt. %; vitamins, 1.08 mg in 100 grams of the product; wherein in 100 grams, the following elements were contained: sodium, 41 mg; potassium, 125 mg; calcium, 60 mg; magnesium, 6 mg; phosphorus, 80 mg; iron, 0. 1 mg. The energy value of the product was determined to be about 23 kilocalories per 100 gram and about $6 \times 10^9$ microorganisms were found to be contained in one gram. This liquid product can be used to feed and treat premature infants.

The curd fraction was found to consist essentially of: water, 83.4 wt. %; total solids, 16.6 wt. %; including: proteins, 6.6 wt. %; fats, 6.0 wt. %; carbohydrates, 2.1 wt. %; organic acids, 1.0 wt. %; ash, 0.9 wt. %; vitamins, 1.43 mg in 100 grams. The energy value was determined to be about 92 kilocalories per 100 grams and about $6 \times 10^8$ microbes were found to be present in one gram of product. The curd fraction alone or with carbohydrates added can be formulated into a liquid or solid food product.

Example 17
Fat-Free Diet Supplement

Ten kg of a fat-free cow milk was heat-treated at 120° C. for 20 minutes and cooled to 39° C. After cooling, 320 grams of symbiotic microorganisms consisting of 80.0 grams of the strain 317/396 of the group Er-2 *Lactobacillus acidophilus* and 240 grams of microorganisms of the strain N.V. Er 317/402 of *Lactobacillus acidophilus* were introduced into the cooled milk. Symbiotic microorganisms were thoroughly mixed and allowed to stand for 46 hours. The fermented product obtained was cooled to 8° C. and again allowed to stand for 18 hours. The product was determined to have an acidity of about 270° Th.

The product was then separated into liquid and curd fractions. The liquid fraction mainly consisted of: water, 94.4 wt. %; total solids, 5.6 wt. %; including: proteins, 0.45 wt. %; fats, 0.05 wt. %; carbohydrates, 1.6 wt. %; organic acids, 3.0 wt. %; ash, 0.5 wt. %; vitamins, 1.54 per 100 grams. The following minerals were determined to be present in 100 grams of the product: sodium, 40 mg; potassium, 120 mg; calcium, 58 mg; magnesium, 14 mg; phosphorus, 75 mg; iron, 0.1 mg. The product was determined to have an energy value of 20 kilocalories per 100 grams.

The curd fraction mainly consisted of: water, 84.3wt. %; dry substances, 15.9 wt. %; including: proteins, 11.0 wt. %; fats, 0.2 wt. %; carbohydrates, 1.6 wt. %; organic acids, 2.0 wt. % and ash, 0.9 wt. %.

Example 18
Powdered Medicinal Agent

The liquid fraction of the product prepared as described in Example 17 was then subjected to freeze-drying at an initial temperature of −50 C., a final temperature of −26° C. and a residual pressure of $13.3 \times 10^3$ Pa for 23 hours.

The resulting dry product mainly consisted of: water, 4.0 wt. %; total solids, 96 wt. %; including: proteins, 7.8 wt. %; fats, 0.5 wt. %; carbohydrates, 32.2 wt. %; organic acids, 50.5 wt. %; ash, 5.0 wt. %; vitamins, 15.4 mg per 100 grams. The following minerals are contained in 100 grams of the product: sodium, 510 mg; potassium, 1,210 mg; calcium, 915 mg; magnesium, 133 mg; phosphorus, 810 mg; iron, 1.1 mg. The product was determined to have an energy value of 346.4 kilocalories per 100 grams. The product was found to possess the same chemical properties even after being stored for two years.

Example 19
Powdered Baby Formula

The liquid fraction of the product prepared as described in Example 16 was subjected to freeze drying at the initial temperature of −50 C, final temperature of −25° C. and a residual pressure of $13.3 \times 10^3$ Pa for 24 hours.

Before reconstitution, the final product mainly consisted of water (4.0 wt. %) and total solids (96.0 wt. %), including: proteins (12.3 wt.%), fats (3.3 wt. %); carbohydrates (58.8 wt. %); organic acids (15.4 wt. %); ashes (5.6 wt. %). 100 grams of the product was determined to contain about 10.86 mg of vitamins and the following minerals (mg): sodium, 390; potassium, 1,275; calcium, 610; magnesium, 51; phosphorus, 802; iron, 1.1. An energy value of 362 kilocalories per 100 grams was determined. One gram of product was estimated to contain about $3.0 \times 10^9$ microorganisms. The powdered product was found to be capable of storage at room temperature for two years without diminishing in its chemical properties. The product can be prepared, for example, as a baby formula.

Example 20
Powdered Fermented Milk Product

The product prepared in Example 3 was subjected to freeze drying at the initial temperature of −50° C., final temperature of −26° C. and a residual pressure of $13.3 \times 10^3$ pa for 24 hours.

The dry product obtained mainly consisted of the following: water, 4.0 wt. %; total solids, 96 wt. %; including: proteins, 34.0 wt. %; fats, 0.6 wt. %; carbohydrates, 47.7 wt. %; organic acids, 7.2 wt. %; mineral substances, 6.8 wt. %. The product was calculated to have an energy value of 352.6 kilocalories per 100 grams and a vitamin content of 9.5 milligrams per 100 grams. The number of microorganisms in one gram of product was determined to be about $2 \times 10^8$. After being stored for more than three months, the product was found to retain its chemical properties.

Example 21
High-Fat Fermented Milk Product

One thousand kg of cow milk containing 6.0 wt.% of fat, 4.0 wt. % of protein and 5.0 wt. % of carbohydrates was sterilized at 98° C. for five minutes, cooled to 36° C., then 20 kg of symbiotic microorganisms consisting of 4 kg of the 317/392 strain of Er-2 *Lactobacillus acidophilus* and 16 kg of the strain N.V. Er 317/402 of *Lactobacillus acidophilus* were introduced. The symbiotic microorganisms were thoroughly mixed with the milk and allowed to stand at a 36° C. temperature for 5.5 hours. The fermented product obtained was cooled to 6° C. and again allowed to stand for 12 hours.

The resulting product was determined to have an acidity of about 65° Th (0.5850% lactic acid) and to consist mainly of: water, 84.2 wt. %; total solids, 15.8 wt. %; including: proteins, , 4.0 wt. %; fats, 6.0 wt. %; carbohydrates, 4.1 wt. %; organic acids, etc., 0.9 wt. % and ash 0.8 wt. %. 100 grams of the product was determined to contain the following minerals: sodium, 41 mg; potassium, 120 mg; calcium, 130 mg; magnesium, 14 mg; phosphorus, 80 mg; iron, 0.1 mg.; and 2.54 milligrams of vitamins. The energy value of the product was determined to be 90.0 kilocalories per 100 grams. $4 \times 10^8$ of microorganisms were contained in 1 gram of product.

Example 22
High-Energy Powdered Fermented Milk Product

The product prepared in Example 21 was subjected to freeze drying at an initial temperature of −50° C., final temperature of −26° C. and a residual pressure of $13.3 \times 10^3$ Pa for 23 hours. The product was stored for more than 2 years without losing chemico-biological properties.

The dry product consisted essentially of: water, 4.0 wt. %; total solids, 96.0 wt. %; including: proteins, 24.3 wt. %; fats, 36 wt. %; carbohydrates, 24.4 wt. %; organic acids, etc., 5.5 wt. %; ash, 5.8 wt. %. 10.3 mg of vitamins and the following minerals: sodium, 400 mg; potassium, 1,200 mg; calcium, 1,200 mg; magnesium, 120 mg; phosphorus, 800 mg; iron, 1.0 mg were contained in 100 grams of product. The energy value of the product was 540 kilocalories per 100 grams and $2 \times 10^8$ microorganisms were contained in one gram.

Example 23
Topically Administered Fermented Milk Nutraceutical

The effect of topical administration of a fermented milk product prepared as described above was studied using 24 Chinchilla rabbits. Standard skin-facial wounds of about 2×2.5 cm (500 sq. mm) in size were inflicted in the back area of all the rabbits; a skin graft was dissected with subcutaneous fat and fascia up to a muscular layer, wound edges containing subcutaneous muscle were crushed with Kocher's forceps. Following hemeostasis, rabbits were infected by introducing 1 ml microbial suspension containing $1.5 \times 10^9$ Staphylococcus aureus into the wound. 48 hours postinfection, the treated animals revealed a pronounced purulent inflammation.

All animals were divided into three groups each containing eight rabbits. In group I (test), the animals were treated with the fermented milk. For comparison, rabbits of Group II were treated with Rivanol (Chinosolfabrik, Germany). Group III consisted of control, untreated animals. Treatment was initiated on the third day postinfection. The fermented milk preparations were applied locally using liberally wetted, loosely placed napkins onto the wound followed by application of an aseptic dressing. Animals of the control group were maintained under identical conditions, and were subjected to daily wound sanitation and application of aseptic dressings.

The clinical course of wound healing was controlled based on a number of criteria-nature and amount of the discharge, terms for arresting a perifocal inflammatory reaction, necrolysis terms, emergence of granulations, epithelization, terms of a wound healing. At the same time, the surface area of the wound was measured; cytological, morphological studies of the wound edge and bottom were carried out; and bacteriological studies of wound discharge (prior and during the treatment) were performed. To determine the presence of microbes in sections, the preparations were Gram-Weigart stained. Bacteriological studies were carried out with regard to a rate and duration of Staphylococcus dissemination from a destruction focus. The following quantitative characteristics of dissemination were used: up to 25 colonies on a Petri dish =limited growth; up to 70 colonies=poor growth; up to 200 colonies=abundant growth; and more than 200 colonies=complete growth.

Material from a purulent wound was removed with a calcined and quenched standard loop, 3 mm in diameter, emulsified in 1 ml saline and then plated by 0.05ml onto Petri dishes of plain agar. The plated material was placed in an incubator at 37° C. for 18–20 hours followed by Staphylococcus aureus colony count.

When the degree of wound healing among the three groups of animals was compared (Table I), it was revealed that the processes of necrolysis, emergence of first granulations and epithelization and cupping of the inflammatory reaction in a wound occurred in Group I much earlier than in Groups II and III, with complete wound healing in Group I proceeding relatively faster (on the average, twice as fast as in control groups). Analysis of the results of bacteriological studies on purulent wound discharge show that the topically administered fermented milk product resulted in high antibacterial efficiency when compared with the Rivanol treated and control groups.

TABLE 1

|  | Number of Animals | First granulation advent, days | Full wound healing, days | Edge epithelization advent, days | Full wound filling with granules, days | Full wound healing, days |
| --- | --- | --- | --- | --- | --- | --- |
| Fermented milk product | 8 | 3.375 | 6.1 | 7.5 | 10.5 | 14.6 |
| Rivanol | 8 | 7.0 | 13.5 | 15.1 | 18.9 | 24.7 |
| Control | 8 | 8.9 | 17.5 | 19.6 | 23.0 | 29.0 |

Histological and histochemical studies of wound healing on the 5th day of treatment demonstrated that there was a pronounced bacterial contamination of wounds against a background of drastic inflammatory changes in deep layers in animals of the control group.

On the 10th day, inflammatory changes with an abundant microflora were revealed in the wound surface and deep layers. There were foci of necrosis, microabscesses in the subcutaneous fat, a purulent skin infiltration encompassing areas of the conserved epidermis and subcutaneous fat of the wound edges.

On the 15th day, there was a relative weakening of the intensity of the inflammatory process as compared to the preceding period and a thinning of the granular-fibrinous layer on the wound surface were observed. A new growth epithelium from the wound edges creeped over, with a thin layer, a granulation tissue. A pronounced purulent infiltration with necrotic changes and the emergence of purulent fusion foci (microabscesses) were revealed in the surface layers of the granulation tissue as well as in the subsurface tissues. Round-cell infiltrates of mainly a lymphophagocytic nature, single macrophages, phagocyte leukocytes were formed around a pronounced capillary network.

The use of the claimed fermented milk product greatly accelerated reparative processes in wounds: thus, by the 5th day of treatment, a marked thinning of a granular-fibrinous layer was observed with a decrease in the number of stab neutrophile leukocytes and a cupping of the inflammatory process in tissues adjacent to a wound. A comparative clearing of the wound cavity from necrotic areas and fibrinopurulent impositions was observable with the prevalence of a serious component in the pus mass. A considerable expansion of granulation tissue was also observable.

On the 10–15th day, reparative processes in the wound were expressed far stronger over the control group. Thus, by the 15th day, in a majority of cases, a complete reconstitution of an epithelial coat on the wound surface was observable with a tendency to thickening and recovering of all layers. A surface layer of the granulation tissue was represented by a fine-fibrous connective tissue with a papillary excrescence, whereas a deep layer was represented by a coarse-fibered fibrous tissue. A differentiation of vessels into arterioles and venules took place.

The study of cicatrices in animals of all three groups has shown that those in Group I were characterized by a uniform epithelial lining with the reconstitution of all layers thereof, and in deep layers—by an ordered disposition of thin, gentle collagenous fibers the bundles of which had a horizontal arrangement. In animals of Group II, a more coarse cicatricial tissue prevailed, in some places with the absence of the epithelial coat and a more disordered disposition of collagenous fibers in the fibrous connective tissue. In rabbits of Group III, a cicatrix was presented by a coarse fibrous tissue on the surface of which elements of skin were absent, connective-tissue fibers in deeper layers had a disordered disposition, phenomena of sclerosis, single foci of a chronic infection in the form of granulomas with single staphylococci took place.

Thus, these studies show that metabolites of lactic acid bacteria of the claimed invention, when applied locally on the purulent wound models under experimental conditions in rabbits, contribute to faster wound cleaning from necrotic tissues and pyogenic microflora, stimulate the regeneration processes in wounds and shorten the time required for wound healing, thus promoting wound healing with a soft, elastic cicatrix.

Example 24
Orally Administered Fermented Milk Nutraceutical

A fermented milk product prepared as described above was orally administered to 1,427 sick and healthy human carriers of pathogenic microorganisms. No side-effects were associated with consumption.

During a three-month period (once a month), carriers of a Strepto-staphylococcal infection were subjected to a bacteriological study and remained under observation during a year (once every three months), and a bacteriological study of the nasopharyngeal ring was performed.

Carriers of a strepto-staphylococcal infection were divided into two groups, one of which was treated with antibiotics, the other group was treated with the claimed fermented milk product by intranasal administration of a dose of 0.5 ml three times a day for five days. Following administration of the fermented milk product, a measuring of two nasal front sections was conducted.

Within a two-month period of observations, among those patients who had received the claimed product, 0.8% remained as infection carriers, whereas 2.2% of those who received antibiotics remained carriers.

Patients suffering from pyo-inflammatory diseases of urinary bladder and urethra were treated with the claimed fermented milk having an 165° Th (1.4850% lactic acid) acidity. The treatment procedure was as follows: The fermented milk product containing not more than 0.1 wt. % of fat in accordance with the present invention, was introduced into the cavity of the urinary bladder (via Pezzer or Nelaton catheter), as well as directly into the urethra. Exposure time was 60–120 minutes, product temperature was 37–40° C. Patients with suprapubic vesicle fistulas were given the claimed product in the amount of 70–100 ml for 10–12 days; patients with cystitis, 100–150 ml for 7–10 days; patients with urethritis, 10–15 ml for 8–10 days.

Eighty-five patients were treated by the said method. The control group consisted of 50 patients treated by conventional medicinal methods. Patients treated with the claimed product have revealed a number of significant advantages: improvement of a general condition, loss of painful feelings, pronounced reduction of dysuric effects, body temperature normalization, cessation of discharge, wound granulation improvement. These changes usually appeared on the 9th day of treatment. Laboratory studies have revealed a shift of urine pH from alkaline to acidic (urine pH was reduced from 8 to 7 with 62% of patients of the control group and in the test group—pH has reduced from 8 to 5.4 with 87% patients, $P<0.01$). Leukocyturia was markedly decreased (2.4 times with 57% of patients of the control group and 5.0 times with 23% of patients of the test group, $P<0.01$). Decrease of proteinuria was also observed ($P<0.02$). Bacteriuria, when treated conventionally, was reduced from 5–10 million to 500,000 to one million microbial cells in 1 ml of urine with 53% of patients. Following treatment with the claimed product, bacteriuria has reduced to 5,000–50,000 with 76% of patients ($P<0.02$). There was no evidence of a growth of pathogenic microorganisms with 15% of patients.

Example 25
Gynecological Benefits of Fermented Milk Nutraceuticals

The fermented milk product (10–20 ml) was administered every day for 8–15 days to 186 girls, 165 gynecological patients, 64 women in labor and puerperal and 157 pregnant women were trated antenatally. The treatment protocols for the girls was repeated in a month. The treatment's effectiveness was monitored using a variety of clinico-laboratory methods, which included visual observations, colpopexy, bacterioscopic and bacteriological studies.

One hundred seventy-two (172) samples from the vagina and 84 from the cervical canal were subjected to a bacteriological study. Of the vaginal samples studied, 91.7% of the gynecological patients revealed both a pathogenic and opportunistic-pathogenic microflora, as well as Candida yeast infection. In a majority of cases, clusters of microbes were present.

A course of colpitis with pregnant women, often proceeded without symptoms wherein two-thirds of pregnant women revealed stage IV of purity of the vaginal flora and more than 2–3 kinds of microbe associations. The remaining third of the examined patients (39.5%) revealed a combination of an opportunistic-pathogenic microflora pathogenic Staphylococci, Proteus, some serotypes of *Escherichia coli* and Candida yeast).

In the group of women in labor with a prolonged (more than 24 hours) water-free period, when studied bacteriologically, a massive dissemination in the cervical canal was found with 23 from 28 puerperas, opportunistic and pathogenic microflora were isolated in 82.1% cases, in particular *Staphylococcus aureus* (46.7%). The analysis of the results of treating gynecological patients and pregnant women on the completion of the first treatment course showed that, without exception, there was a considerable improvement of clinical manifestations, a substantial reduction of the number of leukocytes, and a complete loss of yeast cells.

Bacteriological studies of gynecological patients showed a drastic decrease (83.4%) in the amount of opportunistic and pathogenic microflora with a primary prevalence of rod-shaped bacteria. Bacterioscopic studies of smears revealed a change in the purity of vaginal flora with the transitions from the fourth stage to the second. The microflora of pregnant women was reduced by about 75% due to the administration of the fermented milk product.

The results obtained in these studies support the use of the claimed liquid fermented milk product for beneficial obstetric-and-gynecological results. The use of the claimed fermented milk with an 120 Th (1.0800% lactic acid) acidity in a liquid form produces a high therapeutic effect in a child's gynecology. Dropping the claimed product into vaginas of girls by means of individual pipettes (during 15–20 days) and introducing into the area of the posterior vault of the vagina of adult women in the amount of 10–20 ml for 8–15 days showed a considerable improvement of clinical manifestations, a drastic reduction of a number of leukocytes and a microflora dissemination from 70.8% prior to treatment to 34.2% post treatment as well as the loss of a pathogenic microflora and normalization of vaginal biocenosis.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method of therapy or prophylaxis of a disease or condition, which is associated with or caused or contributed to by an opportunistic or pathogenic microorganism in a subject, comprising administering to the subject an effective amount of a culture of a *Lactobacillus ocidoophilus* from the Er 2 group.

2. A method of claim 1, wherein said culture additionally comprises *Lactobacillits acidophilus* N.V. Er 317/402.

3. A method of claim 1 wherein the strain of the group Er-2 is selected from the group consisting of: 317/381, 317/393, 317/401, 317/396, 317/395, 317/392, 317/402 and 317/389.

4. A method of claim 1, wherein the culture comprises at least one strain of a *Lactobacillus acidolphilus* from the Er-2 group and a *Lactobacillus acidolphilus* from the strain N.V. Er 317/402, wherein the ratio of the N.V. Er 317/402 strain to the group Er-2 strain is selected from the group consisting of 1:1, 2:1, 3:1 and 4:1.

5. A method of claim 1, wherein the culture further comprises a *Lactobacillus salivarius* strain.

6. A method of claim 1, wherein the culture is contained in a fermented milk product.

7. A method of claim 6, wherein the fermented milk product is selected from the group consisting of: an infant formula, a fermented milk drink and a thickened semi-solid or solid composition.

8. A method of claim 7, wherein the thickened semi-solid or solid composition is selected from the group consisting of: yogurt, curd and ice cream.

9. A method of claim 1, wherein the culture is prepared as a powder.

10. A method of claim 1, wherein the disease or condition is selected from the group consisting of gastrointestinal disease, hemolytic jaundice, wound infection, omphalitis, otitis, vaginitis, urethritis, bladder infection, allergy, sinusitis, rhinitis, high serum cholesterol, atrophy, dystrophy, sepsis, colon cancer, rectal cancer and breast cancer.

11. A method of claim 1, wherein the culture is topically applied.

12. A method of claim 11, wherein the culture is prepared as an ointment, tincture, cream, gel, solution, lotion, spray, suspension or suppository.

* * * * *